US00PP20273P2

(12) United States Plant Patent
Radler

(10) Patent No.: US PP20,273 P2
(45) Date of Patent: Sep. 8, 2009

(54) SHRUB ROSE PLANT NAMED 'RADWHITE'

(50) Latin Name: *Rosa hybrida*
Varietal Denomination: Radwhite

(75) Inventor: William J. Radler, Greenfield, WI (US)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 12/216,128

(22) Filed: Jun. 30, 2008

(51) Int. Cl.
*A01H 5/00* (2006.01)

(52) U.S. Cl. ..... Plt./103

(58) Field of Classification Search ..... Plt./103, Plt./104
See application file for complete search history.

*Primary Examiner*—Annette H Para
(74) *Attorney, Agent, or Firm*—Buchanan Ingersoll & Rooney PC

(57) ABSTRACT

A new and distinct shrub rose plant is provided that abundantly and substantially continuously forms attractive single blossoms that initially are light yellow in coloration and change to white when fully mature. The plant exhibits vigorous vegetation and a bushy growth habit. The foliage is dark green with a matte finish. Excellent resistance to blackspot has been experienced. The plant is well suited for growing as attractive ornamentation in parks and gardens.

1 Drawing Sheet

Botanical/commercial classification: *Rosa hybrida*/shrub rose plant.

Varietal denomination: cv. Radwhite.

SUMMARY OF THE INVENTION

The new variety of *Rosa hybrida* shrub rose plant of the present invention was created at Greenfield, Wis., U.S.A., by artificial pollination wherein two parents were crossed which previously had been studied in the hope that they would contribute the desired characteristics. The female parent (i.e., the seed parent) was the 'Radmom' variety (non-patented in the United States). The 'Radmom' variety is an open pollinated seedling of the 'Bucbi' variety (U.S. Plant Pat. No. 4,225) which is being marketed under the CAREFREE BEAUTY trademark. The male parent (i.e., the pollen parent) of the new variety was the 'Radsweet' variety (non-patented in the United States). The parentage of the new variety can be summarized as follows:

'Radmom'×'Radsweet'.

The seeds resulting from the above pollination were sown and small plants were obtained which were physically and biologically different from each other. Selective study resulted in the identification of a single plant of the new variety.

It was found that the new shrub rose plant of the present invention possesses the following combination of characteristics:

(a) abundantly and substantially continuously forms attractive single blossoms that initially are light yellow in coloration and change to white when fully mature,
(b) exhibits a round and bushy growth habit,
(c) forms vigorous vegetation,
(d) forms attractive dark green foliage with a matte finish, and
(e) exhibits excellent resistance to blackspot.

A new rose variety is provided which bears white blossoms combined with substantially continuous blooming and blackspot resistance. The blooming cycle is believed to be one of the longest observed to date for a rose plant.

The new variety well meets the needs of the horticultural industry. It can be grown to advantage as ornamentation in parks, gardens, public areas, and in residential settings. The new variety is particularly well suited for providing attractive ornamentation in the landscape. The white blossoms contrast nicely with the matte dark green foliage.

The new variety of the present invention also can be readily distinguished from its ancestors. More specifically, the 'Radmom' variety displays very pale pink buds and white blossoms, and the 'Radsweet' variety forms light pink blossoms that commonly fade to near white. The new variety of the present invention also can be readily distinguished from the 'Sea Foam' variety (U.S. Plant Pat. No. 2,463) which displays dissimilar double blossoms and a shorter growth habit than the new variety.

Additionally, the new variety can be readily distinguished from the 'Radrazz' variety (U.S. Plant Pat. No. 11,836) and the 'Meipotal' variety (U.S. Plant Pat. No. 8,841 upon an inspection of the blossom color. The blossoms of the 'Radrazz' variety are cherry red in coloration, and those of the 'Meipotal' variety are pink with white eyes.

The characteristics of the new variety have been found at Waso, Calif., U.S.A., to be homogeneous and stable and to be strictly transmissible by asexual propagation, such as budding, grafting, and the rooting of cuttings from one generation to another. The new variety reproduces in a true-to-type manner by such asexual propagation.

The new variety has been named 'Radwhite' and will be marketed in the United States under the WHITE OUT trademark.

BRIEF DESCRIPTION OF THE PHOTOGRAPH

The accompanying photograph shows, as nearly true as it is reasonably possible to make the same in a color illustration of this character, a typical flowering plant of the new variety. The illustrated rose plant of the new variety was approximately four years of age and was observed during June while growing outdoors near West Grove, Pa., U.S.A.

DETAILED DESCRIPTION

The chart used in the identification of colors is that of The Royal Horticultural Society (R.H.S. Colour Chart), London, England. The description is based on the observation of two-year-old specimens of the new variety during May while growing in containers in a greenhouse near West Grove, Pa., U.S.A.

Class: Landscape shrub.

Plant:

*Height.*—Approximately 3.5feet on average at the end of the growing season.

*Width.*—Approximately 3.5 feet on average at the end of one growing season.

*Habit.*—Round and bushy.

Branches:

*Color.*—Young stems: near Yellow-Green Group 146C with some Greyed-Orange Group 174A. Adult wood: Greyed-Purple Group 184A and Yellow-Green Group 145A at the leaf nodes.

*Thorns.*—Size: approximately 1 cm in length, approximately 2 mm in diameter at the base, and less than 1 mm in diameter at the apex.

Leaves:

*Leaflets.*—Number: 3, 5, and 7. Length: approximately 3.5 cm on average for a terminal leaflet, and approximately 3 cm on average for a lower leaflet. Width: approximately 2.5 cm on average for a terminal leaflet, and approximately 2 cm on average for a lower leaflet. Shape: ovate with a rounded base and an acuminate tip. Margins: double serrate. Texture: smooth on both surfaces and with a coarse midrib on the under surface. Overall appearance: attractive dark green matte leaves. Color (young foliage): Upper surface: Green Group 143C. Under surface: Yellow Green Group 144B. Color (adult foliage): Upper surface: Green Group 137A. Under surface: Green Group 138B, and commonly with some Greyed-Purple Group 183C at the margins.

Inflorescence:

*Number of flowers.*—Commonly approximately 5 blooms on average in a cluster.

*Peduncle.*—Near Green Group 138B, commonly approximately 8 mm in length, and approximately 6 mm in diameter.

*Sepals.*—Upper surface: smooth and glabrous, and commonly Yellow-Green Group 138B in coloration. Under surface: smooth and Green Group 138B in coloration. Size: commonly approximately 2.5 cm in length on average, and approximately 0.5 cm in width at the base. Number: five.

*Buds.*—Shape: pointed at tip. Length: approximately 2.5 cm on average as the calyx breaks. Diameter: approximately 1.5 cm as the calyx breaks. Color: Yellow Group 11C.

*Flower.*—Form: single. Shape: informal. Diameter: approximately 7 cm on average when fully open. Color (when opening begins): Upper surface: near Yellow-Orange Group 15D at the base and near Yellow Group 11D at the apex. Under surface: Yellow-Orange Group 16D at the base and Yellow Group 11D at the apex. Color (at end of blooming): Upper surface: Yellow-White Group 158D. Under surface: Yellow-White Group 158D. Fragrance: commonly slightly fragrant when opening, and non-fragrant when fully open. Petal number: approximately 10 on average. Petal drop: the petals commonly do not readily detach. Stamen number: approximately 85 to 90 on average, and regularly arranged about the pistils. Anthers: Yellow-Orange Group 22A in coloration. Filaments: approximately 5 to 10 mm in length, and Yellow Group 5C in coloration. Pistils: separate and free, and commonly number approximately 27 on average. Stigmas: Yellow Group 13C in coloration. Styles: Red Group 45B in coloration. Receptacle: achenes are present on the bottom wall.

Development:

*Vegetation.*—Vigorous and strong.

*Blossoming.*—Abundant and substantially continuous during the growing season.

*Resistance to diseases.*—Excellent with respect to blackspot as well as to rust when compared to other commercial varieties under comparable growing conditions near West Grove, Pa., U.S.A.

*Formation of hips/seeds.*—Sparse.

I claim:

1. A new and distinct shrub rose plant characterized by the following combination of characteristics:

(a) abundantly and substantially continuously forms attractive single blossoms that initially are light yellow in coloration and change to white when fully mature, (b) exhibits a round and bushy growth habit, (c) forms vigorous vegetation, (d) forms attractive dark green foliage with a matte finish, and (e) exhibits excellent resistance to blackspot; substantially as herein shown and described.

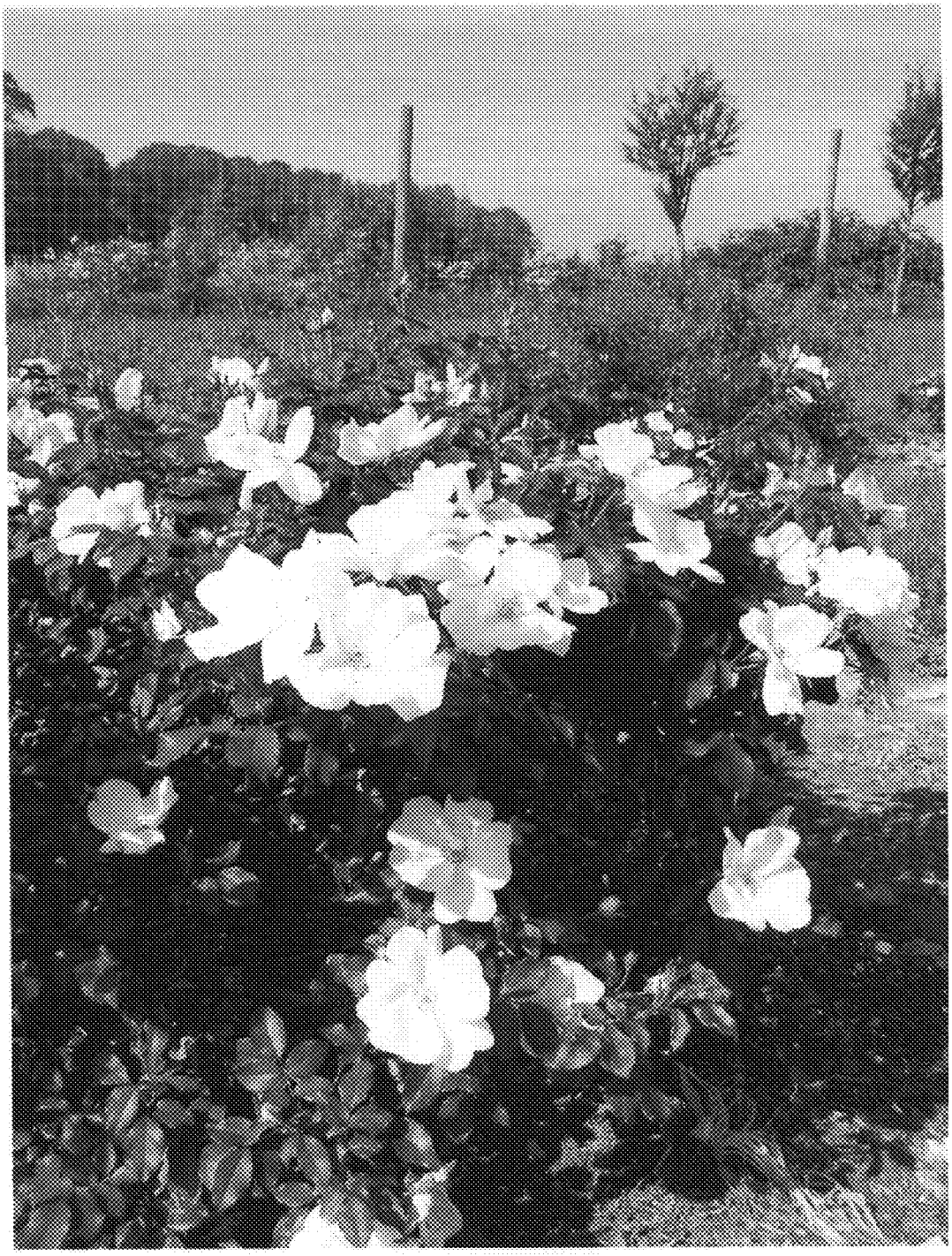

* * * * *